(12) United States Patent
Steinbarger et al.

(10) Patent No.: US 6,994,732 B2
(45) Date of Patent: Feb. 7, 2006

(54) PROSTHETIC ANNULAR COUPLING SOCKET ADAPTOR WITH ADJUSTABLE CLAMP

(75) Inventors: Steve Steinbarger, Willmington, OH (US); Damon Johncour, Raleigh, NC (US)

(73) Assignee: Prosthetic Design, Inc., Clayton, OH (US)

( * ) Notice: Subject to any disclaimer, the term of this patent is extended or adjusted under 35 U.S.C. 154(b) by 159 days.

(21) Appl. No.: 10/377,289

(22) Filed: Feb. 28, 2003

(65) Prior Publication Data

US 2003/0220701 A1 Nov. 27, 2003

Related U.S. Application Data

(60) Provisional application No. 60/361,427, filed on Feb. 28, 2002.

(51) Int. Cl.
*A61F 2/74* (2006.01)
(52) U.S. Cl. .................................................. 623/27
(58) Field of Classification Search .................. 623/27, 623/28, 32, 38
See application file for complete search history.

(56) References Cited

U.S. PATENT DOCUMENTS

| 5,201,775 A | * | 4/1993 | Arbogast et al. | 623/38 |
| 6,334,876 B1 | * | 1/2002 | Perkins | 623/34 |
| 6,458,163 B1 | * | 10/2002 | Slemker et al. | 623/38 |
| 2002/0147500 A1 | * | 10/2002 | Wilkinson et al. | 623/35 |

* cited by examiner

*Primary Examiner*—David J. Isabella
*Assistant Examiner*—William H Matthews
(74) *Attorney, Agent, or Firm*—Taft, Stettinius & Hollister, LLP (57) ABSTRACT

A prosthetic coupling comprising an annular coupling adapter having a coupling end and an opposed pylon mounting end, the coupling end including a central bore adapted to receive, and be coupled to a prosthetic limb pyramid component, where the pylon mounting end includes a diametrically restrictable tube with at least two circumferential discontinuities and an axial depth with a predetermined extension greater than a minimum depth required to adequately secure a prosthetic limb pylon component therein, where the predetermined extension provides the prosthetic coupling height adjustability with respect to the prosthetic limb pylon to which it is adapted to be secured. Such prosthetic couplings may be supplemented with bushings inserted within the pylon mounting end to inhibit further pylon insertion beyond a desired depth.

15 Claims, 7 Drawing Sheets

PROSTHETIC ANNULAR COUPLING SOCKET ADAPTOR WITH ADJUSTABLE CLAMP

CROSS REFERENCE TO RELATED APPLICATION

This application claims the benefit of U.S. Provisional Application Ser. No. 60/361,427, entitled, "PROSTHETIC ANNULAR COUPLING SOCKET ADAPTOR WITH ADJUSTABLE CLAMP", filed on Feb. 28, 2002, the disclosure of which is incorporated herein by reference.

BACKGROUND

1. Field of the Invention

The present invention relates to prosthetic devices, and more particularly, to prosthetic couplings having annular coupling socket adapters (aka, "pyramid receivers") with adjustable height tube clamps.

2. Description of the Related Art

Figure 1:
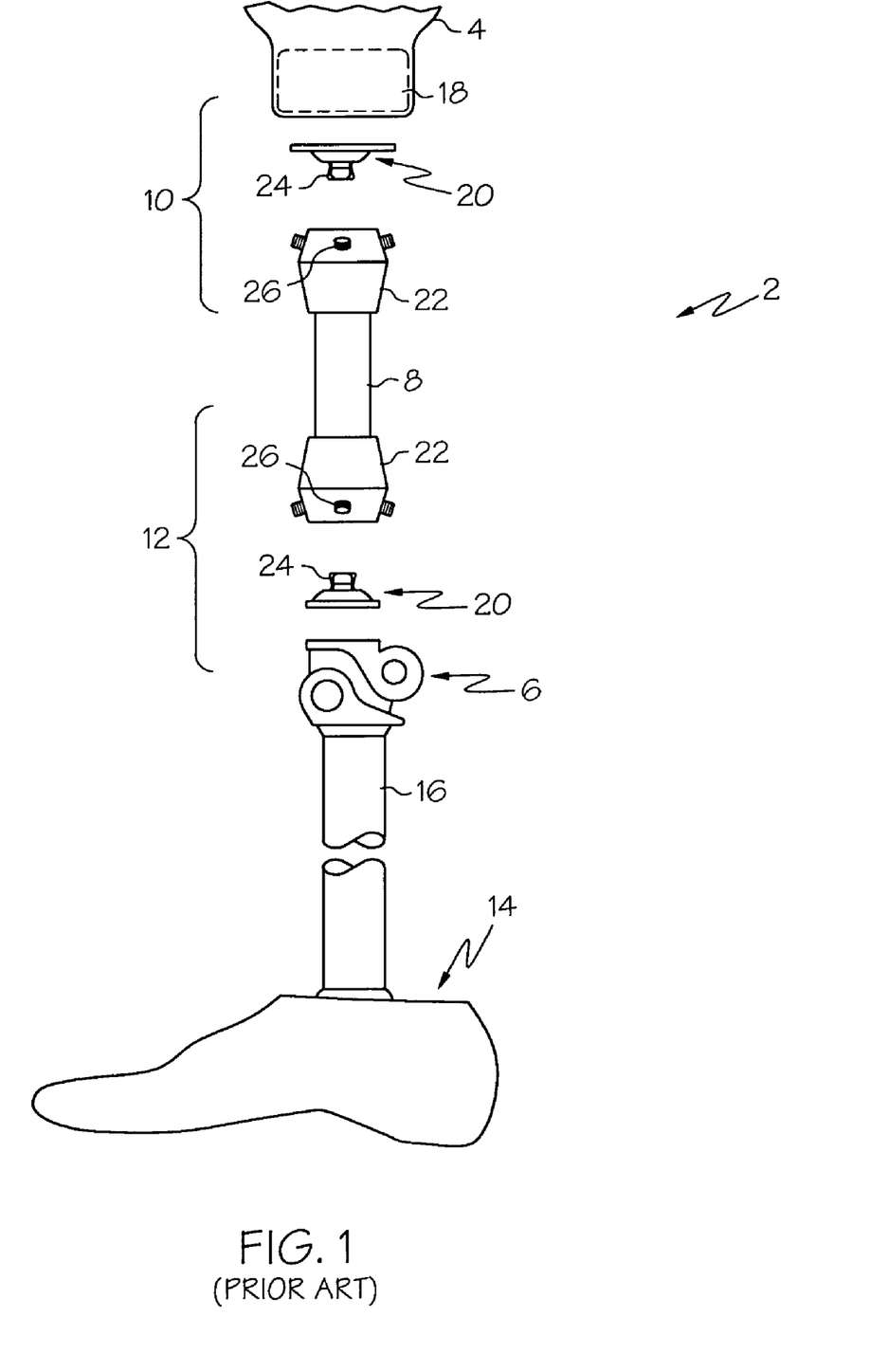
FIG. 1 is a perspective view of a prior art prosthetic limb assembly.

As shown in FIG. 1, an example of an above-knee ("AK") prosthetic limb 2 for a patient may include a prosthetic limb socket 4 for receiving the wearer's residual limb, a knee joint assembly 6, a first pylon 8 coupled between the prosthetic limb socket 4 and the knee joint assembly 6, interconnection components 10 for coupling the first pylon 8 to the prosthetic limb socket 4, interconnection components 12 for coupling the first pylon 8 to the knee joint assembly 6, an ankle/foot assembly 14, and a second pylon 16 coupled between the knee joint assembly 6 and the ankle/foot assembly 14. The interconnection components 10 may consist of a locking or suction assembly 18 (such as, for example, a Shuttle Lock component commercially available from Prosthetic Design, Inc.) positioned within a distal end of the prosthetic limb socket 4, the conventional pyramidal link-plate 20, and a pyramid receiver 22 for coupling the first pylon 8 to the distal boss 24 of the pyramidal link-plate 20. Likewise, the interconnection components 12 may consist of the conventional pyramidal link-plate 20 mounted to the knee joint assembly 6 and another pyramid receiver 22 for coupling the first pylon 8 to the distal boss 24 of the pyramidal link-plate 20. The plurality of set screws 26 are tightened, thus securely mounting the pyramidal link-plate 20 to the pyramid receiver 22.

Figure 2:
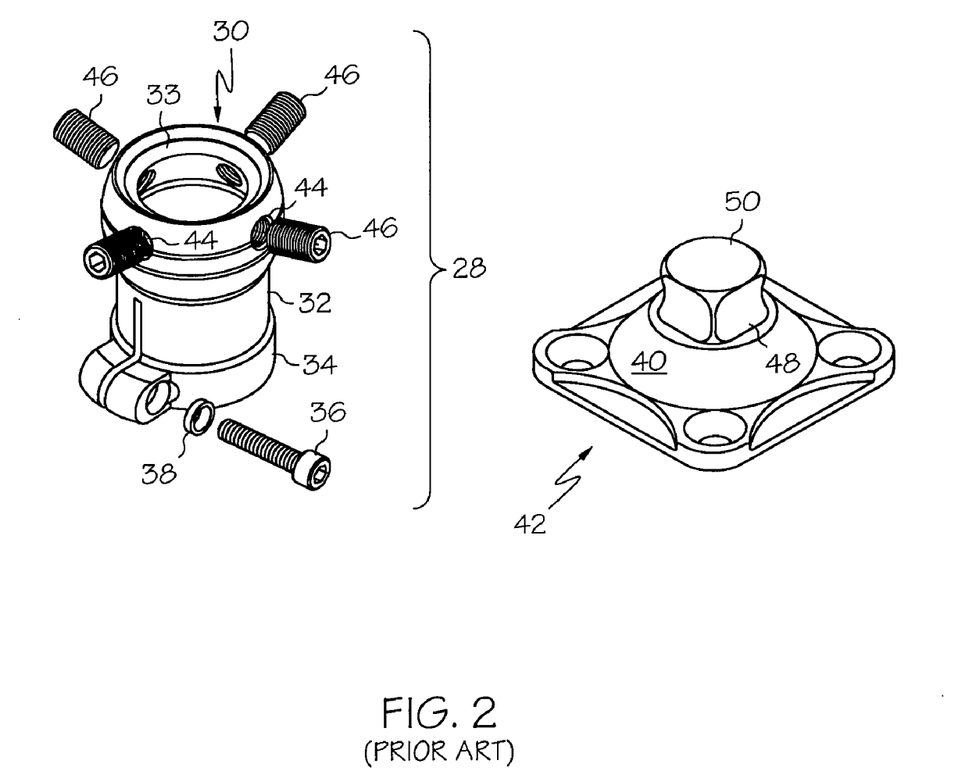
FIG. 2 is a perspective view of a prior art pyramid receiver.
Figure 3:
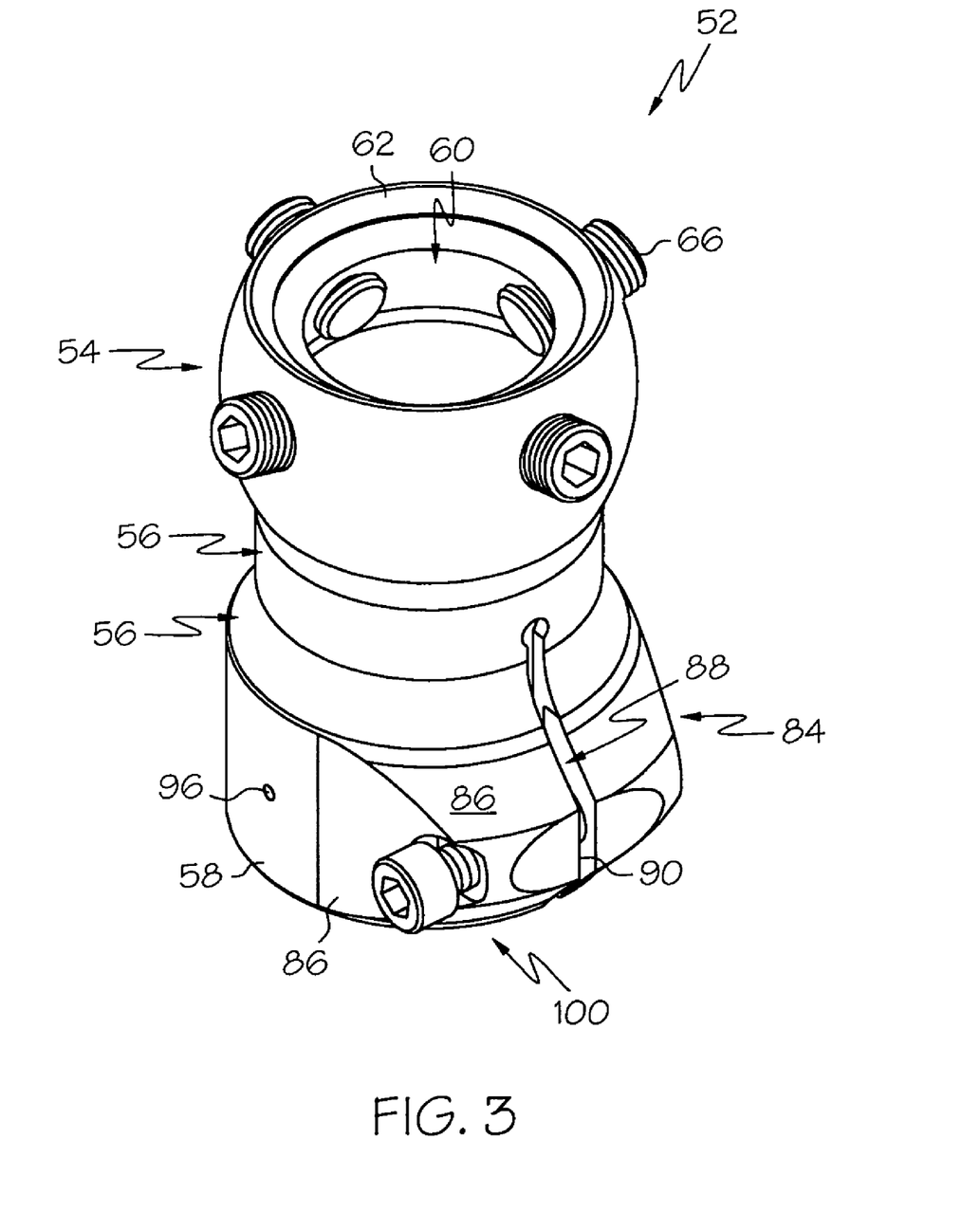
FIG. 3 is a perspective view of a first exemplary embodiment of the present invention.

As shown in FIG. 2, a prior art prosthetic pyramid receiver 22 includes a pyramid receiver portion 30 and a diametrically restrictable tube portion 32. The tube portion 32 includes a ring-clamp 34, a screw 36 and a washer, 38. The pyramid receiver portion 30 has a concave upper mouth 33 adapted to mate with the domed structure 40 of a pyramid 42. Angled holes 44 extend from the exterior surface and continue inward, thereafter extending into the interior channel of the pyramid receiver portion 30. These holes 44 are adapted to receive set screws 46 for throughput. When tightened to engage the surfaces 48 of the frustropyramidal boss 50, the pyramid 42 is pulled toward the pyramid receiver portion 30 until the domed structure 40 of the pyramid 42 engages the concave upper mouth 33 of the pyramid receiver portion 30. Thereafter, further movement between the domed structure 40 of the pyramid 42 and the concave upper portion 33 of the pyramid receiver portion 30 is minimal (collectively the elements). Further tightening of the set screws 46 increases the amount of force required axially to move the elements in relation to one another, eventually "locking" the elements together for all intents and purposes.

In fitting prosthetic limbs to patients, it is often necessary for the prosthetist to modify the lengths and/or orientations of various prosthetic limb components with respect to each other during initial fitting, or after the patient has worn the prosthetic limb for a period of time. The prosthetist attempts to maintain the alignment of the prosthetic components along the TKA line; a line parallel to the trochanter, knee and ankle. A pylon, in particular, is capable of being ground down or cut so as to shorten the length of the pylon to accord proper fitting. Problems sometimes arise when the pylon is ground down or cut, thereby shortening its length beyond that which is required. This necessitates the procurement of a completely new pylon. Alternatively, if the original pylon is too short, the current state of the art provides no alternative for the prosthetist other than procuring another pylon having a greater length.

Accordingly, there is a need for a pyramid receiver and associated tube clamp that provides axial height adjustability with respect to pylon length. Alternatively, there is a need for a system in which a prosthetist may simply exchange different height spacers or bushings to be placed within the tube of the tube clamp, between an axial shoulder in the tube and the end of the pylon, to adjust the height of the pyramid receiver with respect to the pylon.

SUMMARY OF THE INVENTION

In a first exemplary embodiment of the present invention, a height-adjustable prosthetic coupling is provided that has an annular coupling adapter (pyramid receiver) on one end and a diametrically restrictable tube (tube clamp) on the opposing end, which allows for height (axial) adjustment between the coupling and a prosthetic pylon. The diametrically restrictable tube has an internal depth which accommodates the insertion of a portion of the pylon. Conventional pyramid-receiver tube clamps have a diametrically restrictable tube of a minimal length sufficient to provide enough surface area to securely lock the tube clamp onto the pylon. One reason for minimizing this length is to reduce the material costs for such components. The first exemplary embodiment of the present invention, on the other hand, provides a diametrically restrictable tube having an internal depth which can accommodate more than the minimum length of the pylon necessary for properly securing the pylon to the coupling. In other words, the interior height of the tube is greater than prior art tubes. When the patient requires the overall length between the tube clamp and pylon to be adjusted, the prosthetist "frees up" the diametrically restrictable tube so as to enable movement between the internal surface of the tube and the exterior surface of the pylon. Once the desired overall length is reached, the prosthetist restricts the diametrically restrictable tube and prevents noticeable movement between the pylon and tube; both in the vertical, and in the rotational/axial direction. Thus, the present invention provides for human errors in measuring and provides adjustability to meet the patient's needs and may not require the procurement of a plurality of pylons of varied lengths.

Likewise, the elements of the first exemplary embodiment may be combined with bushings (or spacers) that fill any potential axial void that may be present in the first exemplary embodiment between the shoulder of the coupling extending radially into the channel of the tube and the longitudinal end-surface of the pylon; resulting in a second exemplary embodiment. The second exemplary embodiment provides a plurality of variable-height axial bushings that are insertable into the tube of the coupling before the pylon is inserted. One or more of these bushings may be inserted to fill any potential void between the coupling and the longitudinal surface of the pylon. Thus, the adjustment of the prosthetic components may be made easier for the prosthetist because the weight of the tube clamp and associated prosthetic components may be pressed onto the pylon without the fear of hampering the measurements surrounding the proper depth of the pylon.

It is a first aspect of the present invention to provide a prosthetic coupling comprising an annular coupling adapter having a coupling end and an opposed pylon mounting end, the coupling end including a central bore adapted to receive, and be coupled to a prosthetic limb pyramid component, where the pylon mounting end includes a diametrically restrictable tube with at least two circumferential discontinuities and an axial depth with a predetermined extension greater than a minimum depth required to adequately secure a prosthetic limb pylon component therein, where the predetermined extension provides the prosthetic coupling height adjustability with respect to the prosthetic limb pylon to which it is adapted to be secured.

It is a second aspect of the present invention to provide an adjustable prosthetic coupling comprising a pylon receiving end having an inner ring for captively engaging a prosthetic pylon therein, the inner ring including at least two arcuate segments being diametrically constrictable, an outer ring circumscribing the inner ring and, a prosthetic component interface end for engaging and securing a prosthetic component thereto, where the pylon receiving end accommodates varying depths of insertion of the prosthetic pylon beyond the minimum required for secured fitting to enable height adjustability.

It is a third aspect of the present invention to provide an adjustable prosthetic coupling comprising a pylon receiving portion having a means for selectively securing a prosthetic pylon therein and, a pyramid receiving portion including a means for selectively securing a prosthetic pyramid thereto, where the means for selectively securing the prosthetic pylon therein includes a plurality of height adjustments between the prosthetic pyramid and the prosthetic pylon, and the means for selectively securing the prosthetic pylon therein enables day-to-day use.

It is a fourth aspect of the present invention to provide a method for custom fitting prosthetic devices, comprising the steps of: providing a prosthetic coupling device adapted to couple a prosthetic pylon to a second prosthetic limb component, the coupling device having a concavity adapted to interface with a prosthetic pylon, the cavity accommodating various depths of pylon insertion to provide height adjustability with the second prosthetic limb component, the coupling device further being designed for day-to-day use; and, mounting the prosthetic component to the prosthetic pylon so as to provide a secure coupling between the prosthetic component enabling day-to-day use.

DETAILED DESCRIPTION OF THE PREFERRED EMBODIMENTS

The exemplary embodiments of the present invention are described and illustrated below as prosthetic limb couplings, for mounting a first prosthetic component to a second pylon component, that include height-adjustable tube clamps for mating with pylon components. The various orientational or positional terms used to describe the elements of the inventions are therefore used according to this frame of reference. Of course, it will be apparent to those of ordinary skill in the art that the preferred embodiments may also be used in combination with one or more prosthetic components to function as a complete prosthetic assembly. In such a case, the orientational or positional terms may be different. However, for clarity and precision, only a single orientational or positional reference will be utilized; and, therefore it will be understood that the positional and orientational terms used to describe the elements of the exemplary embodiments of the present invention are only used to describe the elements in relation to one another. For example, a pylon will have two opposing longitudinal surfaces; one being characterized as proximal, while the other is characterized as distal. Yet, the pylon may be rotated in space, thereafter transforming the proximal end into the distal end and vice versa without departing from the scope and spirit of the present invention.

As shown in FIGS. 3–8, a first exemplary embodiment of the present invention 52 provides a prosthetic coupling 52 having a titanium pyramid receiver 54 on the proximal end, and a titanium tube 56 on the distal end with an aluminum ring clamp 58 mounted thereto. The pyramid receiver 54 has a proximal opening with a mouth 60 having a conical interior surface 61 that is machined or molded to mate with a "male" prosthetic limb component such as, for example, a conventional prosthetic pyramid 62. The pyramid receiver 54 also includes at least two diametrically opposed holes 64 angled distally in relation to an imaginary planar surface parallel to the proximal end of the pyramid receiver 54. Each angled hole 64 may be machined or molded to house a single set screw 66; the set screws maybe 5/16–18 socket head set screws.

Referencing FIG. 2, the pyramid 42 includes a frustropyramidal, four-sided boss 50 projecting from a domed shaped, or spherically convex base 40 (hereafter domed portion). The pyramid 42 is secured to another prosthetic component with four screws (a standard industry design). These four screws attach the pyramid 42 firmly to a prosthetic component (not shown) and provide structural support at the proximal end for connection between the prosthetic pyramid 42 and the prosthetic pyramid receiver 54.

Mounting the pyramid 42 to the pyramid receiver 54 begins by placing the frustropyramidal boss 50 within the concave mouth 60 of the pyramid receiver proximal opening so as to enable the set screws 66 to engage the faces 48 of the frustropyramidal boss 50. Concurrently, as the set screws 66 are engaging the faces 48 of the frustropyramidal boss 50, the domed portion 40 of the pyramid 42 is being moved closer to the concave mouth 60 of the pyramid receiver 54. As the pyramid 42 comes in close proximity to the pyramid receiver's 54 interior conical surface 62, the exterior surface of the domed portion 40 abuts the conical interior surface 62 of the pyramid receiver 54 and a friction fit results. The tighter the set screws 66 push against the faces 48 of the frustropyramidal boss 50, the relatively better the friction fit. In other words, the higher the force the set screws 66 exert against the faces 48 of the frustropyramidal boss 50, thus pushing the pyramid 42 against the pyramid receiver 54, the greater the amount of force required to unseat the pyramidal receiver's 54 interior conical surface 62 from the domed portion 40 of the pyramid 42. This results in relatively no movement between the two elements in either the vertical or rotational direction when the set screws 66 are sufficiently tightened.

Figure 4:
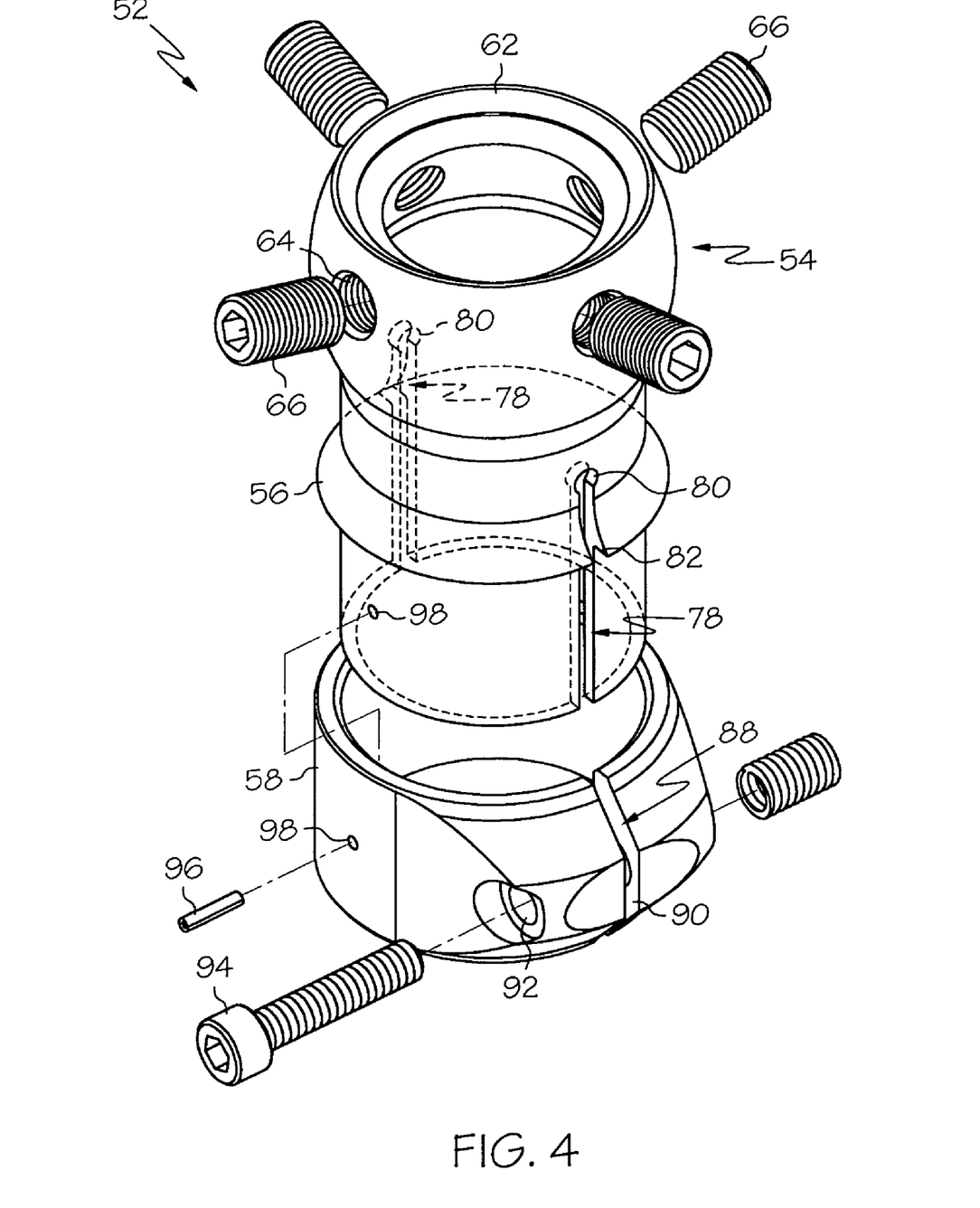
FIG. 4 is an exploded view of the first exemplary embodiment of the present invention.
Figure 5:
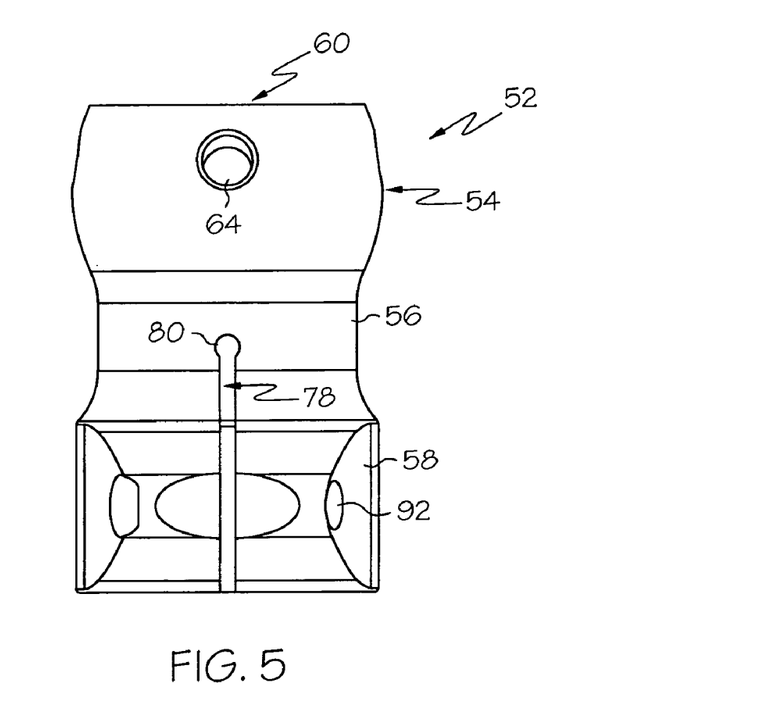
FIG. 5 is a frontal view of the first exemplary embodiment of the present invention.
Figure 6:
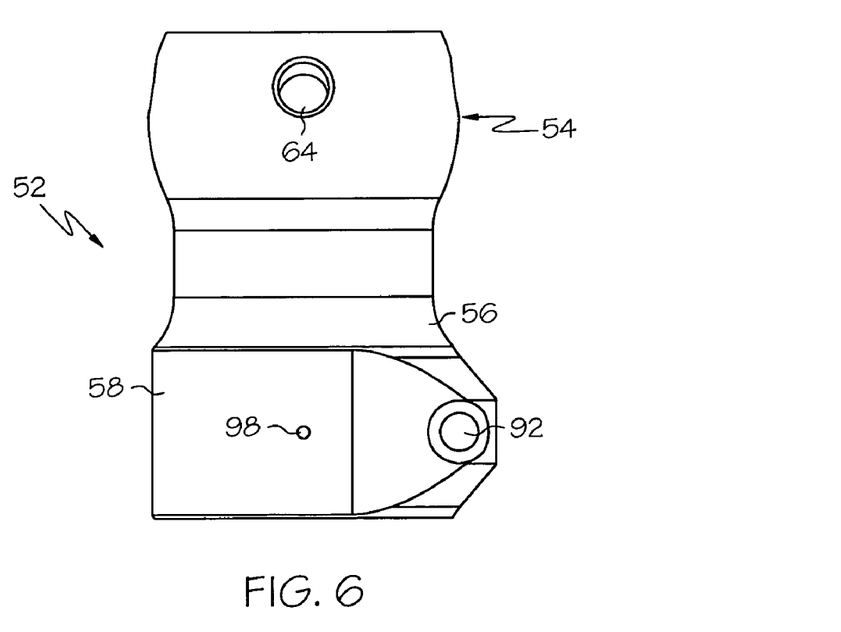
FIG. 6 is a left side view of the first exemplary embodiment of the present invention.
Figure 7:
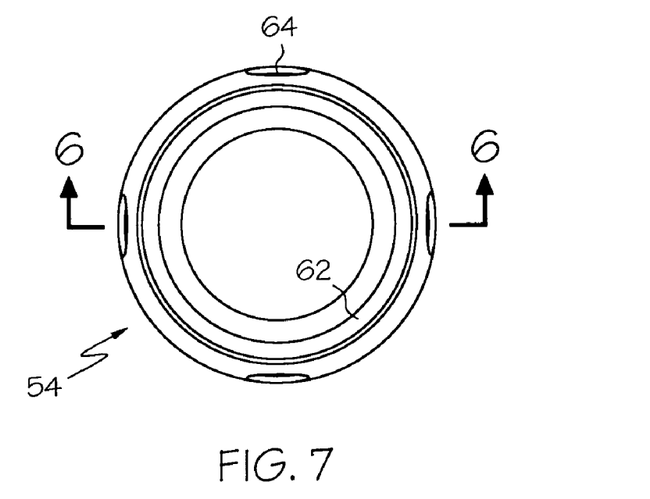
FIG. 7 is an overhead view of the first exemplary embodiment of the present invention.
Figure 8:
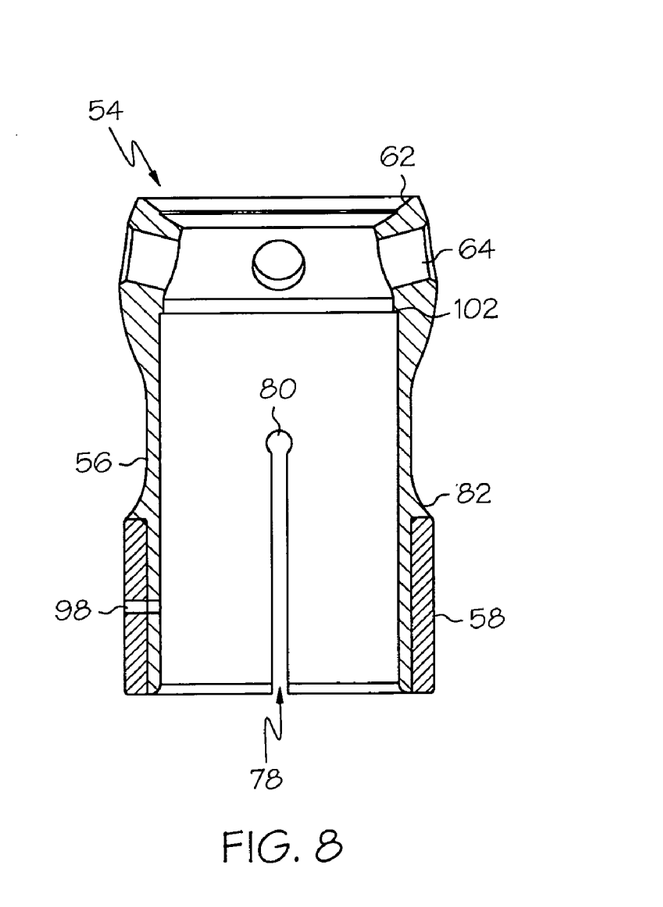
FIG. 8 is a cross sectional view of the first exemplary embodiment of the present invention along lines 6—6 of FIG. 7.

As shown in FIG. 4, the tube 56 includes two discontinuities in the form of channels 78 extending therethrough and upward from a distal end thereof, which separate at least two circumferential portions of the tube 56 from one another. The channels 78 terminate with the formation of a stress riser 80 to dissipate stress and inhibit the formation or a stress crack at the point of termination. These channels 78 are in part what provides the flexibility of the tube 56 to conform to a plurality of internal diameters, thereby supplemented by the adjustable aluminum ring clamp 58 which provides the restrictive force. The exterior of the tube 56 includes a lip or shoulder 82 extending radially from the tube 56 that is adapted to abut the proximal surface of the ring-clamp 58. Extending distally from the lip 82, the outer circumferential surface of the tube 56 is recessed to mate with the inner diameter of the ring clamp 58.

The restrictable aspect of the ring clamp 58 includes a radial projection 84 that takes on a pyramidal shape which exhibits an apex in exterior diameter at the axial center of the clamp and diminishes proportionally in the vertical and radial directions accordingly, thus providing an outer surface 86 which slopes in the axial as well as distal and proximal directions. A break 88 effectively bisects the radial projection of the ring clamp 58, providing complimentary, mirror image planar surfaces 90 parallel to the TKA line. Perpendicular to the break 88 of the ring clamp 58 is a hole 92 which extends through the pyramid shaped radial projection 94 of the ring clamp 58. The hole 92 extends through the complimentary parallel planar surfaces 90 created by the break 88. This hole 92 may be machined or molded so as to accept a threaded device such as a screw 94; the screw may be a #10–32 socket head cap screw. The screw 94 facilitates the restrictive force necessary to bring the parallel surfaces 90 of the ring clamp 58 closer together than compared to equilibrium without the screw 94, such that the internal diameter of the tube 56 at the distal end becomes variable; generally smaller in diameter when restrictive force is applied.

It is preferred, but not necessary, that the adjustable aluminum ring clamp 58 be mounted on the distal end of the hollow titanium tube 56. One example of how this might be accomplished is by way of a retention pin 96 that is friction fit within a hole 98 radially bored through the ring clamp 58 and the tube 56. When the retention pin 96 is in place, free rotation and axial separation of the ring clamp 58 from the tube 56 is inhibited. In any such mounting technique, it is preferred, but not necessary, to align the break 88 with at least one channel 78.

An inner concavity 100 of the tube 56 provides a "female" interface between the coupling 52 and a second prosthetic component such as, for example, a graphite pylon. The interior surface of the tube 56 which makes contact with the exterior surface of the pylon (not shown) may be smooth or of non-uniform texture and include a taper approximating its distal end to effectively provide a maximum axial depth for insertion of the pylon. In this exemplary embodiment, the maximum axial depth is one-half inch longer than the minimum depth necessary to provide sufficient surface area to achieve secure locking (as required by the ISO 10328 torque test) between the coupling 52 and the pylon. This additional one-half inch depth of the tube 56 provides height adjustability for the component as will be discussed further below.

The pylon is generally a cylindrical shaft having a uniform circular cross section. The pylon has two longitudinal end surfaces which make up the respective distal and proximal ends of the pylon. Assembly of the pylon into the tube 56 of the coupling 52 begins by inserting the proximal end of the pylon into the tube 56 until the pylon abuts the shoulder 102 inside of the tube 56. Using a paint marker, the exposed portion of the pylon immediately adjacent to the ring-clamp is marked. The pylon may then be withdrawn from the tube 56 up to one-half inch by sliding the coupling 52 away from the pylon; all the while providing at least the minimum pylon insertion depth. This minimal pylon insertion depth being the depth at which enough of the exterior surface of the pylon is in potential contact with enough of the interior surface of the tube 56 such that a resulting friction fit between the two elements will disallow substantial rotational and/or vertical movement between the two during day-to-day use of the prosthetic limb by the patient. Thereafter, the ring clamp 58 is restricted by use of the screw 94. An application of Loctite® may be applied before tightening the screw to help maintain the proper restrictive force.

Alternatively, to adjust the pylon to coupling 52 distance, the prosthetist may simply measure down from the proximal longitudinal surface of the pylon and mark the exterior surface of the pylon corresponding to the minimum insertion depth. Thereafter, the prosthetist may make vertical adjustments of the pylon so long as the marked exterior surface of the pylon is inserted into the tube 56.

Additionally, the prosthetist may adjust the pylon length after the initial fitting of the patient's prosthetic components. In this case, the prosthetist begins by loosening the ring clamp 58 around the tube 56, thus enabling vertical and/or rotational movement between the coupling 52 and the pylon. Next, the prosthetist simply pulls a portion of the pylon out from the tube 56, up to one-half inch until the proper measurements are met if the distance is too short; conversely, the prosthetist simply pushes a portion of the pylon into the tube 56, up to one-half inch until the proper measurements are met if the distance is too great; all the while keeping the minimum amount of exterior pylon surface in potential contact with the minimum amount of interior surface of the tube 56 such that a friction fit between the two elements will be maintained with proper tightening of the ring clamp 58. While the prosthetist is adjusting the length between the distal end of the pylon and the proximal end of the coupling 52, it will be recognized by one of ordinary skill in the art that other concerns may be addressed by the prosthetist such as alignment retention of the prosthetic components attached to either the distal end of the pylon, or the proximal end of the coupling 52. Finally, the prosthetist tightens the ring clamp 58 by torquing the screw 94 to the setting recommended by the manufacturer and the adjustment is complete.

As a caveat to the aforementioned procedure for adjustability, it will also be recognized by one of ordinary skill in the art that if the amount of the pylon inserted into the tube is the minimum amount necessary for a proper friction fit, adjustability to a greater length may require: the procurement of another pylon having a longer length; adjusting the prosthetic component mounted to the distal end of the pylon; or, exchanging a coupling 52 having a greater tube 56 height.

It will be apparent to those of ordinary skill that the one-half inch extension of the tube of the tube clamp provided in the first exemplary embodiment is not limiting, and it is within the scope of the invention to provide extensions having longer or shorter lengths as desired.

The ring clamp 58 may be of the same or a similar material or of an alloy comprising one or more of the materials of the tube 56 and/or pyramid receiver 54. Materials suitable for use in the fabrication of the tube 56, the pyramid receiver 54, and the ring-clamp include elemental metals, alloys of elemental metals, composites, and any other similar materials. It is preferred that the material chosen for the tube 56 inhibits any permanent deformation attributable to the ring clamp 58.

It is likewise within the scope and spirit of the invention to provide grooves on the outer circumferential surface of the tube 56 that mate with corresponding grooves in the ring clamp 58 to align the ring-clamp 98 to the proper exterior surface of the tube 56, thus maintaining the ring clamp's 58 axial position around the tube 56 when the ring clamp 58 is not sufficiently tightened.

In the first exemplary embodiment 52, the clamp is separate from the manufacture of the tube 56. However, it is within the scope and spirit of the present invention to provide a titanium ring clamp 58 incorporated into the tube 56 and/or pyramid receiver 54.

It is also within the scope and spirit of the present invention to provide a set of bushings or spacers having incremental axial height and uniform circular cross section. In this embodiment, these bushings may be inserted into the tube 56 whenever the measurements taken by the prosthetist indicate that the proximal end of the pylon will not abut the shoulder 102 within the tube 56. The prosthetist begins by making a measurement of the overall length desired as measured from the distal end of the pylon to the proximal end of the coupling 52. Next, the prosthetist marks or measures how much of the pylon will be inserted into the tube 56 for proper fitting. If this measurement is less than the height of the tube 56 available for pylon insertion, the prosthetist simply chooses a bushing having a height to make up the difference. It will be understood by those of ordinary skill in the art that the bushings do not act to provide a friction fit between the pylon and the tube 56, but simply occupy a space or void that would normally be vacant. It is also within the scope of the invention that all or some of the spacers have equal height and are designed to be stackable upon one another.

Another exemplary embodiment of the present invention provides a plurality of couplings 52 having incremental tube heights. This "set" of tube clamps, being interchangeable, provides a prosthetist flexibility regarding adjustments to the length between the proximal end of the coupling and the distal end of the pylon (overall length). As characterized above, this flexibility in tube height does not negate the requirement of a minimum pylon insertion depth for proper friction fitting. The set of couplings may be manufactured with any tube height for pylon insertion, so long as the set as a whole provides incremental adjustment of the overall length at least ranging one-half inch.

Figure 9:
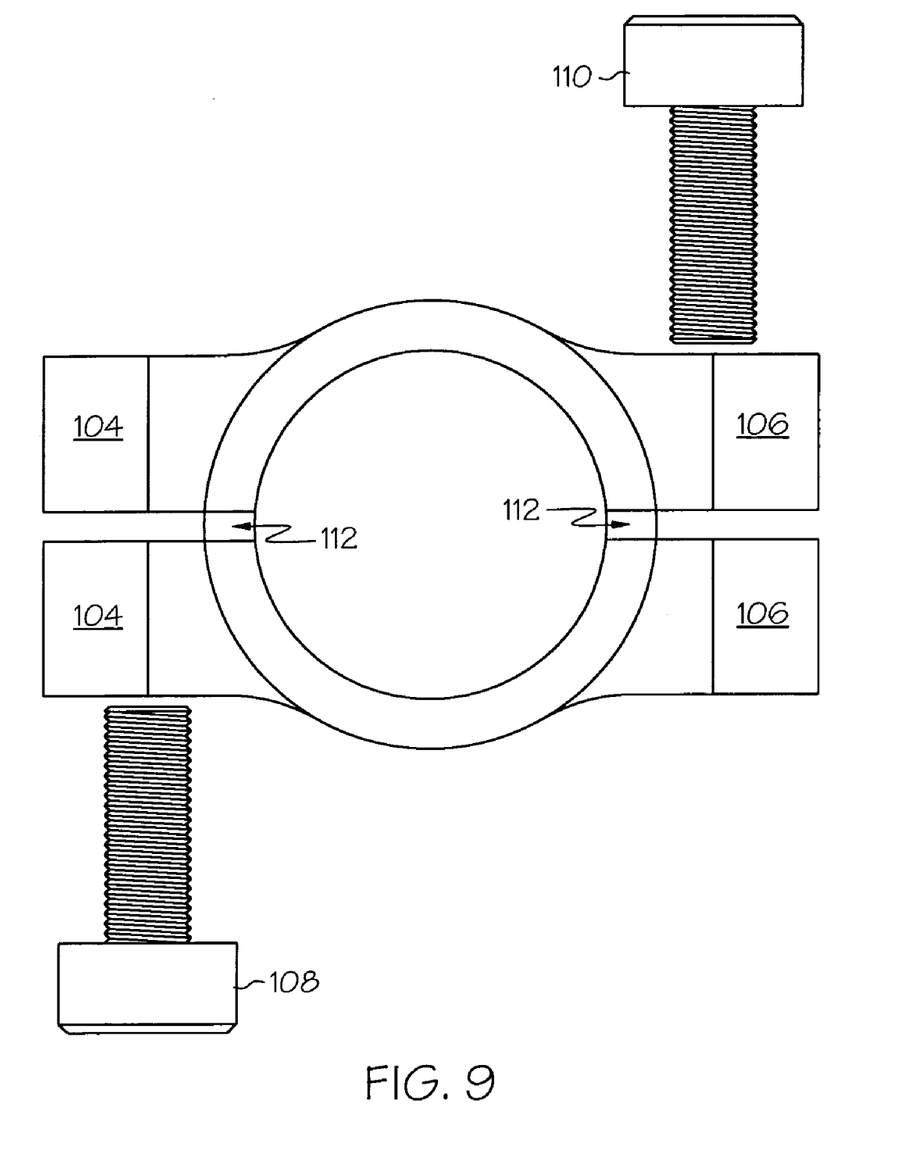
FIG. 9 is an underneath view of an alternate exemplary embodiment of the present invention having two integrated tube clamps.

Still another exemplary embodiment of the present invention is shown in FIG. 9. This exemplary embodiment provides two integrated clamps 104, 106 as part of the tube portion of the coupling. Each clamp includes a set screw 108, 110 that provides the restrictive force necessary to diminish the gaps 112 in the coupling conform the tube portion around a pylon thereby providing a friction fit sufficient to enable day-to-day use of the coupling by a patient. It is also within the scope of the invention to provide a set of couplings embodying such a dual clamp configuration that may be manufactured with any tube height for pylon insertion, so long as the set as a whole provides incremental adjustment of the overall length at least ranging one-half inch.

Adjustability typically requires that the prior art tube clamp be loosened by the prosthetist enabling vertical and/or rotational movement between the pylon and tube clamp, so that measurement can be made to adjust the length/height of the pylon. However, using a set of couplings having incremental pylon insertion depths, the pylon is not adjusted. A prosthetist would remove the pylon and replace the coupling with another coupling having a different pylon insertion depth so as to provide the proper overall length for the patient. The pylon is thereafter inserted into the tube 56 until the proximal longitudinal end of the pylon abuts the shoulder on the inside of the tube. If applicable, other prosthetic components are reattached, all the while cognizant of proper alignment before final attachment and tightening of the screw. Generally, it is envisioned that this set be used without using the bushings as described above. However, it is within the scope and spirit of the present invention to also utilize the bushings if found advantageous by the prosthetist.

If the prosthetist utilizes the set, bushings may be used in lieu of, or in addition to, the next or greater incremental sized coupling in the set. Here, adjustability starts with the prosthetist simply pulling a portion of the pylon out from the tube until the proper measurements are established if the current distance has been determined as being too short. All the while keeping the minimum amount of exterior pylon surface in potential contact with the minimum amount of interior surface (not shown) of the tube such that a friction fit between the two elements will be maintained with proper tightening of the screw. While the prosthetist is adjusting the length between the distal end of the pylon and the proximal end of the coupling, it will be recognized by one of ordinary skill in the art that other concerns may additionally be addressed such as alignment retention of the prosthetic components attached to either the distal end of the pylon, or the proximal end of the coupling. Once the proper distance is determined and/or marked, the pylon is removed from the tube. A bushing is inserted into the tube to accord the proper distance. Next, the pylon is inserted into the tube to abut the bushing which abuts the shoulder in the tube. Finally, the prosthetist tightens the clamp by tightening the screw to the proper torque setting recommended by the manufacturer and the adjustment is complete. As a caveat to the aforementioned procedure for adjustability, it will also be recognized by one of ordinary skill in the art that if the amount of the pylon inserted into the tube is the minimum amount necessary for a proper friction fit, adjustability to a greater length will not be possible without the procurement of another pylon having a longer length, or adjusting the prosthetic component attached to the distal end of the pylon, or switching couplings where the second coupling has a longer height tube. In addition, should the prosthetist desire to exchange couplings and utilize bushings, the procedure is analogous with that enunciated above, but begins with removal of the old coupling and insertion of a new coupling from the set.

Following from the above description and invention summaries, it should be apparent to those of ordinary skill in the art that, while the methods and apparatuses herein described constitute exemplary embodiments of the present invention, it is to be understood that the inventions contained herein are not limited to these precise embodiments and that changes may be made to them without departing from the scope of the inventions as defined by the claims. Additionally, it is to be understood that the invention is defined by the claims and it not intended that any limitations or elements describing the exemplary embodiments set forth herein are to be incorporated into the meanings of the claims unless such limitations or elements are explicitly listed in the claims. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A prosthetic coupling comprising:
   an annular coupling adapter having a coupling end and an opposed pylon mounting end, the coupling end including a central bore adapted to receive, and be coupled to a prosthetic limb pyramid component;
   the pylon mounting end including a diametrically restrictable tube with at least two circumferential discontinuities, the diametrically restrictable tube further having an axial depth with a predetermined extension greater than a minimum depth required to adequately secure a prosthetic limb pylon component therein; and
   the predetermined extension providing the prosthetic coupling height adjustability with respect to the prosthetic limb pylon to which it is adapted to be secured;
   wherein the at least two circumferential discontinuities include two vertical grooves extending from the pylon mounting end towards the coupling end, wherein the grooves separate adjacent semiannular segments of the diametrically restrictable tube, whereby the adjacent semiannular segments further approach towards one another when the diametrically restrictable tube is constricted.

2. The prosthetic coupling of claim 1, wherein:
   the coupling end includes at least four openings accommodating throughput of a plurality of set screws for securing the prosthetic limb pyramid component to the prosthetic coupling; and
   the coupling end is concavely contoured to adaptively engage a domed-shaped prosthetic limb pyramid component potentially coming into contact therewith.

3. The prosthetic coupling of claim 1, wherein the at least two circumferential discontinuities have a width of approximately 0.125 inches.

4. The prosthetic coupling of claim 1, further comprising a clamp for diametrically restricting the tube.

5. The prosthetic coupling of claim 4, wherein the tube exhibits an annular recess on its outer surface to accommodate the clamp positioned circumferentially therearound.

6. The prosthetic coupling of claim 5, wherein an exterior surface of the clamp and an exterior surface of the diametrically restrictable tube provides for a relatively fluent transition therebetween.

7. The prosthetic coupling of claim 4, wherein the clamp is substantially annular and is positioned circumferentially around the tube.

8. The prosthetic coupling of claim 7, wherein the clamp is a ring clamp tightenable by a set screw.

9. The prosthetic coupling of claim 7, wherein the clamp is mounted to the diametrically restrictable tube so as to inhibit unrestricted rotation of the clamp about the diametrically restrictable tube.

10. The prosthetic coupling of claim 7, wherein the clamp is mounted to the diametrically restrictable tube and a first end and a second end are separated to provide a clamp circumferential discontinuity, whereby the clamp circumferential discontinuity is aligned with at least one circumferential discontinuity of the diametrically restrictable tube.

11. The prosthetic coupling of claim 1, wherein:
    the annular coupling adapter and the pylon mounting end are each manufactured, at least in port, from a metal; and
    the clamp is manufactured, at least in part, from a metal.

12. The prosthetic coupling of claim 11, wherein:
    the metal for the annular coupling adapter and the pylon mounting end includes at least one of stainless steel and titanium; and
    the metal far the clamp includes at least one of stainless steel, aluminum, and titanium.

13. The prosthetic coupling of claim 11, wherein:
    the axial depth of the diametrically restrictable tube is approximately between 1.375 and 2.5 inches.

14. A prosthetic coupling comprising:
    a unitary annular coupling adapter having a coupling end and an opposed pylon mounting end, the coupling end including a central bore adapted to receive, and be coupled to a prosthetic limb pyramid component;
    a substantially annular clamp positioned circumferentially around a diametrically restrictable tube of the pylon mounting end for diametrically restricting the tube, wherein the clamp is mounted to the diametrically restrictable tube so as to inhibit unrestricted rotation of the clamp about the diametrically restrictable tube; and
    a plug mounted within a hole that pierces the clamp and the diametrically restrictable tube so as to inhibit rotation of the clamp about the diametrically restrictable tube.

15. An adjustable prosthetic coupling comprising:
    a unitary coupling adapter comprising:
       a pylon receiving end having an inner ring for captively engaging a prosthetic pylon therein, and
       a prosthetic component interface end for engaging and securing a prosthetic component thereto:
    an outer ring circumscribing the inner ring; and
    a plug mounted within a hole that pierces the inner ring and the outer ring so as to inhibit rotation of the outer ring about the inner ring;
    wherein the pylon receiving end accommodates varying depths of insertion of the prosthetic pylon beyond the minimum required for secured fitting, thereby enabling height adjustability;
    wherein the inner ring includes at least two segments being constrictable;
    wherein the outer ring is a ring clamp; and
    wherein the ring damn is mounted to the inner ring so as to inhibit unrestricted rotation of the ring clamp about the inner ring.

* * * * *